(12) United States Patent
Roser

(10) Patent No.: US 7,501,493 B2
(45) Date of Patent: *Mar. 10, 2009

(54) DRIED BLOOD FACTOR COMPOSITION COMPRISING TREHALOSE

(75) Inventor: Bruce Joseph Roser, Cambridge (GB)

(73) Assignee: Quadrant Drug Delivery Limited, Nottingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/841,801

(22) Filed: Aug. 20, 2007

(65) Prior Publication Data

US 2008/0039396 A1     Feb. 14, 2008

Related U.S. Application Data

(63) Continuation of application No. 11/690,778, filed on Mar. 23, 2007, which is a continuation of application No. 09/888,734, filed on Jun. 25, 2001, now Pat. No. 7,253,262, which is a continuation of application No. 08/875,796, filed as application No. PCT/GB96/00119 on Jan. 19, 1996, now Pat. No. 6,649,386.

(30) Foreign Application Priority Data

Jan. 19, 1995    (GB)    ................................. 9501040.1

(51) Int. Cl.
*A61K 35/14* (2006.01)
*C07K 1/00* (2006.01)

(52) U.S. Cl. ..................... 530/383; 530/381; 530/384

(58) Field of Classification Search ............... 435/188, 435/2; 530/383, 380, 381, 384; 514/53, 514/777, 188, 2

See application file for complete search history.

(56) References Cited

U.S. PATENT DOCUMENTS

| | | | |
|---|---|---|---|
| 4,495,175 A | 1/1985 | Chavin et al. | |
| 4,758,657 A | 7/1988 | Farb et al. | |
| 4,806,343 A | 2/1989 | Carpenter et al. | |
| 4,891,319 A | 1/1990 | Roser et al. | |
| 5,288,853 A | 2/1994 | Bhattacharva et al. | |
| 5,364,756 A | 11/1994 | Livesey et al. | |
| 5,565,427 A | 10/1996 | Freudenberg | |
| 5,576,291 A | 11/1996 | Curtis et al. | |
| 5,824,780 A * | 10/1998 | Curtis et al. | 530/383 |
| 5,955,448 A * | 9/1999 | Colaco et al. | 514/53 |
| 6,586,573 B1 | 7/2003 | Besman et al. | |
| 6,649,386 B2 * | 11/2003 | Roser | 435/188 |
| 7,220,836 B2 * | 5/2007 | Roser | 530/381 |
| 7,253,262 B2 * | 8/2007 | Roser | 530/383 |

FOREIGN PATENT DOCUMENTS

| | | |
|---|---|---|
| EP | 0 314 095 | 5/1989 |
| EP | 0 315 968 | 5/1989 |
| EP | 0 475 409 | 3/1992 |
| WO | WO-87/00196 | 1/1987 |
| WO | WO-94/07510 | 4/1994 |
| WO | WO-95/01804 | 1/1995 |
| WO | WO-95/07713 | 3/1995 |

OTHER PUBLICATIONS

Roser, BioPharm, 199, 4(8):47-53.*
"AlphaNine SD/Alphanate/Profilnine SD" Internet Citation, <URL:http://www.alphather.com/products/ins_alpha.htm>, retrieved on Jul. 19, 1999, 1 page.
Bundesverband der Pharmazeutischen Industrie E.V.: 'Rote Liste 1994', Editio Cantor, Aulendorf/Wurtt., DE (1994) Monographs 47 021 and 47 022.
Cleland et al., (ed.), "Design and Development Strategies," Chapter 1 in Formulation and Delivery of Proteins and Peptides, American Chemical Society Symposium Series (1994) 567:1-19.
Colaco et al., Bio/Technology (1992) 10(9):1007-1011.
Communication from the European Patent Office for EP 03 002 147.1, dated Nov. 15, 2006, 1 page.

* cited by examiner

*Primary Examiner*—Ruth A Davis
(74) *Attorney, Agent, or Firm*—Morrison & Foerster LLP

(57) ABSTRACT

A method for preparing a stable dried composition of blood factor product containing a stabilizing amount of trehalose in the absence of a stabilizing amount of albumin is disclosed.

7 Claims, No Drawings

DRIED BLOOD FACTOR COMPOSITION COMPRISING TREHALOSE

CROSS-REFERENCE TO RELATED APPLICATIONS

This application is a continuation of U.S. Ser. No. 11/690,778 filed 23 Mar. 2007 which is a continuation of U.S. Ser. No. 09/888,734 filed 25 Jun. 2001 U.S. Pat. No. 7,253,262 which is a continuation of U.S. application Ser. No. 08/875,796 filed 30 Oct. 1998 now U.S. Pat. No. 6,649,386 which is National Stage Entry of PCT/GB96/00119 filed 19 Jan. 1996 and claims benefit of United Kingdom serial number 9501040.1 filed 19 Jan. 1995. The contents of these documents are incorporated herein by reference.

TECHNICAL FIELD

This invention relates to dried compositions of blood factors for reconstitution with water or aqueous solutions.

BACKGROUND ART

Blood factors, particularly Factor VIII and Factor IX, are now the standard treatment for diseases caused by a lack of the appropriate factor, in particular hemophilia. The blood factor has generally been derived from human blood by various extraction techniques, for example as disclosed in EP-A-0083483, or by expression in genetically modified microorganisms, for example as disclosed in EP-A-0160457 and EP-A-0182448.

Blood factor products such as Factor VIII are highly delicate, unstable proteins. They are usually supplied in the form of frozen solutions in an appropriate buffer or, more generally, as freeze-dried powders. Even the freeze-dried powders must be kept cold during storage. In order to stabilize the freeze-dried material, commercial products contain a stabilizing protein, in particular human serum albumin (HSA). It has not been thought possible to prepare a dry blood factor composition which is stable at ambient temperatures and at pasteurization temperatures (e.g., 60° C.) in the absence of HSA. However, the presence of HSA introduces considerable problems of purification since it is essential that the protein is free of viral contamination. The use of recombinant HSA to overcome these problems is expensive.

DISCLOSURE OF THE INVENTION

Trehalose is known to be a highly effective stabilizing agent for delicate proteins, as disclosed in U.S. Pat. No. 4,891,319, enabling proteins to be dried at temperatures above freezing. We have now found that if trehalose is used to stabilize a blood factor product, not only can the product be dried with or without freezing, but also the product is stable even when retained at a temperature of 60° C. for an extended period, in the complete absence of HSA. According to the present invention therefore we provide a stable dried blood factor composition containing a stabilizing amount of trehalose in the absence of albumin.

MODES OF CARRYING OUT THE INVENTION

In general, any stabilizing amount of trehalose may be used and an excess in general causes no problems. Indeed, the presence of trehalose aids the rehydration process and is physiologically acceptable for injection, being rapidly metabolized to glucose. The composition is particularly suited to formulations of Factor VIII, which may also contain appropriate buffering and ion-reinforcing salts, in particular a source of calcium. In general, a ratio of about 1.0 to 1.5 mg of calcium ions per unit of Factor VIII is appropriate.

Other buffering and modifying agents may also be present in the dried material for reconstitution to the injection solution, for example histidine. However, we have found that the level of salts, particularly sodium chloride, present can affect the preservation on drying. It is thought desirable for the commercial product for injection to have an isotonic salt concentration. However, the processing formulations which are freeze-dried are desirably hypertonic, typically containing about 500 mM NaCl (isotonic NaCl=150 mM), as this is considered to help stabilize the blood factor. As a result, commercial freeze-dried formulations generally have a high salt content and are reconstituted for injection with the appropriate amount of sterile water to obtain an isotonic solution.

A considerably reduced salt content is preferred for the dried material of the invention and, in general a solution of about 500 units of Factor VIII per ml to be dried should preferably contain less than 200 mM, e.g., 75 to 150 mM, NaCl, especially about 100 mM, or even lower, e.g., 20 to 50 mM, especially about 22 to 30 mM. Low salt preparations possess a higher dry stability. The dried product can be reconstituted to the desired salt level with a saline solution instead of the conventional water. In general, the molar ratio of trehalose to salt should be above 1:1, especially above 2.5:1, e.g., above 10:1, preferably above 12.5:1.

The dried composition may be obtained by drying an appropriate solution of the blood factor containing the correct proportions of trehalose and other desired components. In general, the solution that is dried should simply contain all the components required in the reconstituted injection solution, although the solution for drying may not necessarily be at the same dilution. Typically, the solution for drying will contain from 1 to 1,000 units of Factor VIII per ml. The methods of drying may include freeze drying, vacuum drying and spray-drying. A particularly preferred method according to the invention comprises vacuum drying at a temperature no greater than 25° C., preferably no greater than 10° C., to form a foam, thus maximizing the exposed surface and the drying effect.

The following examples illustrate the invention further.

EXAMPLE 1

Recombinant Factor VIII was received as a deep frozen solution containing approximately 2,000 to 2,500 units/ml in the manufacturer's high salt buffer. The thawed solution was dialysed against a buffer solution containing 500 mM NaCl, 15 mM $CaCl_2$, and 10 mM histidine at pH 6.8. The dialysed protein was diluted in the same buffer, but with added trehalose, to give a final concentration of 500 units per ml and 10% by weight trehalose at pH 6.8. This solution was vacuum dried in 1 ml aliquots. Vacuum was reduced step-wise from atmospheric to 4 Pa (30 mTorr) to avoid freezing the sample. The temperature of the sample was not allowed to rise above 12° C. until the formation of a foam, after which the temperature was kept below 30° C. Total drying times were 24 to 28 hours.

The samples were stored for 0, 1.5, 3 and 6 months at 40° C. and then reconstituted in 5 ml aliquots of sterile distilled water before being tested for activity. The results are shown in the following table in comparison with a commercial freeze-dried product containing HSA. Both the test and commercial samples have a high salt content. The post-drying results show that with trehalose it is possible to dry Factor VIII successfully in the absence of HSA, but that a high salt content is unsatisfactory for long term storage, even in the presence of HSA.

| Percentage of initial activity | | |
|---|---|---|
| Time (months) | Sample | Commercial Product |
| 0 | 100.0 | 100.0 |
| 1.5 | 86.8 | 95.3 |
| 3 | 75.1 | 71.2 |
| 6 | 76.6 | 63.6 |

EXAMPLE 2

Samples were dried as described in Example 1 but using a buffer formulation comprising 100 mM NaCl, 15 mM CaCl$_2$, 15 mM histidine and 1.27 molar trehalose (48%) and stored at 60° C. before reconstitution. The results are given in the following table, in which the activity is measured on an ACL 100 automated coagulometer (Instrumentation Laboratory SpA, Milan, Italy). The test sample. with a low salt content showed no significant loss of activity on storage. even after four weeks at 60° C.

| Percentage of initial activity recovered | |
|---|---|
| Wet control | 100.0 |
| Post-drying | 95.5 |
| Two weeks | 96.0 |
| Four weeks | 96.8 |

EXAMPLE 3

Two formulations were prepared containing different salt concentrations as shown:

| | Formulation A | Formulation B |
|---|---|---|
| NaCl | 0.13% | 1.03% |
| CaCl$_2$ | 0.011% | 0.011% |
| L-histidine | 0.12% | 0.12% |
| Tris | 0.002% | 0.002% |
| Tween 80 | 0.002% | 0.002% |
| PEG 3350 | 0.004% | 0.004% |
| Trehalose | 7.5% | 7.5% |
| Factor VIII | 50 U/ml | 50 U/ml |
| Water to 100% | | |

10 ml portions of the formulations were dispensed into separate 30 ml vials so as to give a concentration of Factor VIII of 500 units/vial.

Freeze-drying was performed in a Laconco (Lyph-lock 12 stoppering) freeze drier. Initially, the samples were cooled to −40° C. and then placed under vacuum, before being warmed to −35° C. After 80 hours, the samples were warmed at a rate of 2.5° C./h until the shelf temperature reached 25° C. The samples were then kept at 25° C. for two hours before being sealed under vacuum and removed from the drier.

After drying, the samples were rehydrated with 10 ml of water and the concentration of Factor VIII was measured twice (Assays 1 and 2). The results are given in the following table and are expressed as a percentage of the concentration of Factor VIII with respect to the prefill control (which had been frozen at −70° C.). From the results shown, it can be concluded that Factor VIII can be successfully freeze dried in a trehalose based formulation in the absence of HSA.

| Sample | Assay 1 | Assay 2 |
|---|---|---|
| Formulation A | 77% | 85% |
| Formulation B | 91% | 94% |

The invention claimed is:

1. A method for preparing a stable dried composition of a native blood factor suitable for treating hemophilia which method comprises freeze-drying an aliquot of an aqueous solution of said blood factor in the presence of a stabilizing agent comprising trehalose wherein the aliquot is free of albumin.

2. The method of claim 1 wherein said blood factor is plasma derived.

3. The method of claim 1 wherein said blood factor is recombinant.

4. A vial containing a dried native blood factor composition suitable for treating hemophilia comprising a stabilizing amount of trehalose wherein the composition is free of albumin, the composition being
   (a) stable without refrigeration, and
   (b) suitable for reconstitution with water or with an aqueous solution for administration to a hemophilic patient by injection.

5. The vial of claim 4, containing 0.15 to 2.5 mg trehalose per unit of blood factor.

6. The vial of claim 4, wherein said blood factor is recombinant.

7. A method to stabilize a freeze-dried native blood factor composition suitable for treating hemophilia in the absence of albumin, which method comprises providing to said composition a stabilizing amount of trehalose.

* * * * *